United States Patent [19]

Murakami et al.

[11] Patent Number: 5,151,450
[45] Date of Patent: Sep. 29, 1992

[54] ANTIULCER SUBSTANCE

[75] Inventors: Kiyokazu Murakami, Yokohama; Susumu Yokura, Kawagoe, both of Japan

[73] Assignee: Tokyo Tanabe Company, Limited, Tokyo, Japan

[21] Appl. No.: 659,754

[22] Filed: Feb. 21, 1991

[30] Foreign Application Priority Data

Feb. 22, 1990 [JP] Japan .................................. 2-39663

[51] Int. Cl.$^5$ .............................................. A61K 31/12
[52] U.S. Cl. ..................................... 514/690; 568/375; 568/347; 549/525
[58] Field of Search ................ 568/375, 347; 514/690; 549/525

[56] References Cited

U.S. PATENT DOCUMENTS 4,322,357 3/1982 Kanojia .............................. 568/375

OTHER PUBLICATIONS

Chabudzinski et al, Chem. Abst., vol. 70, #125,448q (1972).
Alder et al, Chem. Abst., vol. 84, #122,041u (1976).

Primary Examiner—James H. Reamer
Attorney, Agent, or Firm—McGlew & Tuttle

[57] ABSTRACT

There are provided 4,5-Dihydroxy-2,6,6-trimethyl-2-cyclohepten-1-one, a method for preparing the same and an antiulcer agent containing the same as an effective ingredient.

3 Claims, No Drawings

ANTIULCER SUBSTANCE

BACKGROUND OF THE INVENTION

1. Field of the Invention

This invention relates to an antiulcer agent containing, as an effective ingredient, 4,5-dihydroxy-2,6,6-trimethyl-2-cyclohepten-1-one

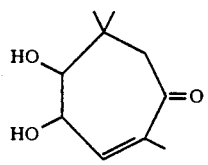

(hereinafter referred to as "Saishin N") obtained from a crude drug "Saishin" (asiasari radix).

2. Description of the Prior Art

"Saishin" is a crude drug described in Japanese Pharmacopoeia as a root and a rootstock of "Usubasaishin" (Asiasarum sieboldii F. Maekana) or "Keirinsaishin" (Asiasarum heterotropoides F. Maekana Var. mandshuricum F. Maekana) which are Aristolochiaceae, stripped of overground portion as much as possible. Saishin is prescribed as an antitussive expectorant or anodyne. As pharmacological effects of Saishin, antiallergic action, cardiac action, sedative action, antipyretic and analgetic actions, and anti-inflammatory action have been known, but there has been not yet reported concerning antiulcer action.

SUMMARY OF THE INVENTION

The present inventors have studied ingredients of crude drugs for a long period of time and as the results, they have found that one of the extracts of Saishin shows antiulcer activity and the active ingredient is Saishin N, and have accomplished the present invention.

According to the present invention, an antiulcer agent containing Saishin N as an active ingredient can be provided.

The Saishin N to be used in the present invention can be produced by extracting Saishin with an organic solvent such as chloroform, and then applying the extract to column chromatography according to stepwise eluting method by using suitable mixed solvents as eluents to effect purification thereof. The mixed solvent can be selected from hexane, chloroform, ethyl acetate and acetone.

Also, Saishin N can be synthesized chemically from eucarvone (2,6,6-trimethylcyclohepta-2,4-dien-1-one).

That is, Saishin N can be synthesized by the step of oxidizing eucarvone to prepare 4,5-epoxy-2,6,6-trimethyl-cyclohepta-2-en-1-one, and the step of subjecting to ring opening reaction by treating with an acid. An oxidizing agent may include organic peracids such as m-chloroperbenzoic acid, perbenzoic acid and permaleic acid; inorganic peracids such as aqueous hydrogen peroxide, perchloric acid, perbromic acid and periodic acid; and oxygen. An acid may include inorganic acids such as perchloric acid, perbromic acid, periodic acid, hydrochloric acid, sulfuric acid and nitric acid; and organic acids such as formic acid, acetic acid, propionic acid, butyric acid, p-toluenesulfonic acid and methanesulfonic acid.

In the present invention, it is needless to say that Saishin N which is extracted from other crude drugs or synthesized by the other synthesis methods can be used.

In the following, inhibitory effects of Saishin N on four kinds of experimental ulcers are described in detail. Each experiment was carried out by using male Wistar rats weighing about 200 g in groups of six, and Saishin N was used by suspending in a 0.5% sodium carboxymethyl cellulose solution. Cetraxate hydrochloride used as a control was also used by dissolving or suspending in the same solution. Activities against respective ulcers were evaluated by an inhibiting ratio obtained by dividing the difference between the ulceration indexes of the non-administered group and the Saishin N group by the non-administered group.

Hydrochloric acid-Ethanol-Induced Erosions

To each rat which had been fasted for 24 hours was orally administered 0.5 ml of a mixed solution of 150 mM hydrochloric acid and 60% ethanol per 100 g of weight. Each rat was slaughtered after one hour, a length of ulcer formed at the fundus gland area of stomach was measured and ulceration index was calculated based thereon. Cetraxate hydrochloride which is a control and Saishin N were each orally administered 30 minutes before administration of a hydrochloride-ethanol mixed solution.

Aspirin-Induced Erosions

In each rat which had been fasted 24 hours, the pyloric end of the stomach was ligated, and simultaneously Saishin N and cetraxate hydrochloride as a control were each administered into duodenum and then 150 mg/kg of aspirin was orally administered after 5 minutes, respectively. After 9 hours from ligation, each rat was slaughtered, a length of ulcer formed at the fundus gland area of stomach was measured and ulceration index was calculated based thereon.

<Water-immersion stress-Induced Erosions>

Each rat which had been fasted for 15 hours was immobilized in a stress cage and immersed chest-deep in a water bath at 21° C. Each rat was slaughtered after 10 hours, a length of ulcer formed at the fundus gland area of stomach was measured and ulceration index was calculated based thereon. Cetraxate hydrochloride as a control and Saishin N were each orally administered 10 minutes before exposure to stress.

Shay's Ulcer

In each rat which had been fasted 48 hours, the pyloric end of the stomach was ligated, and each was kept without giving any food or water for 14 hours. Subsequently, each rat was slaughtered, and area of ulcer formed in the forestomach was measured and ulceration index was calculated based thereon. Cetraxate hydrochloride as a control and Saishin N were each administered into duodenum immediately after ligation.

The results are shown in Table 1.

TABLE 1

|  | Dose mg/kg | Hydrochloric acid-ethanol | Aspirin | Water-immersion stress | Shay |
|---|---|---|---|---|---|
| Saishin N | 20 | 88** | — | — | — |
|  | 50 | 99** | 52** | 49** | — |
|  | 100 | — | 60** | 62** | 49** |
|  | 300 | — | — | — | 58** |

TABLE 1-continued

| | Dose mg/kg | Hydrochloric acid-ethanol | Aspirin | Water-immersion stress | Shay |
|---|---|---|---|---|---|
| Cetraxate hydrochloride | 300 | 86** | 33* | 45* | 11 |

*: P < 0.05
**: P < 0.01

As clearly seen from Table 1, it can be admitted that Saishin N has an extremely excellent antiulcer activity.

Now, an effect on gastric acid secretion of Saishin N is described in detail.

Gastric acid secretion inhibitory effect of Saishin N was tested with male Wistar rats, weighing about 200 g, in groups of six. In each rat which had been fasted 24 hours, the pyloric end of the stomach was ligated, 10 to 100 mg/kg of Saishin N was administered, and total acidity of gastric juice of each rat was measured after 4 hours. Saishin N was administered into duodenum immediately after ligation by suspending in a 0.5% sodium carboxymethyl cellulose aqueous solution. Gastric juice was collected by slaughtering each rat and laparotomizing. Total acidity of the gastric juice was measured by titrating the gastric juice with a 0.1N sodium hydroxide aqueous solution until a pH of the gastric juice reaches 7.0. As a control experiment, total acidity of the gastric juice of an untreated group was also measured in the same manner as described above.

The results are shown in Table 2.

TABLE 2

| | Dose mg/kg | Gastric acid secretion ml | Titrated 0.1 N NaOH ml | Total acidity $\mu$Eq/4 hr | pH |
|---|---|---|---|---|---|
| Control | | 6.6 | 1.00 | 660 | 1.32 |
| Saishin N | 50 | 7.0 | 0.96 | 672 | 1.30 |
| | 100 | 6.5 | 0.95 | 618 | 1.31 |

As clearly seen from Table 2, Saishin N does not show any gastric acid secretion-inhibitory activity. Accordingly, antiulcer effect of Saishin N comes from its cytoprotective activity.

Acute Toxicity

Using 6-weeks old male SD rats, minimum lethal dose (MLD) of Saishin N was examined. As the results, the MLD value was 1000 mg/kg or more in oral administration.

When considering the above experimental results, it can be said that a drug containing Saishin N as an effective ingredient is an excellent antiulcer agent. A dose of Saishin N to a patient may vary depending on age, conditions, etc., but is generally 1 to 1000 mg, preferably 10 to 600 mg per day for an adult in oral administration, and it is preferably administered by dividing into 1 to 6 times, more preferably 1 to 3 times.

In the present invention, by admixing conventional pharmaceutical carriers to Saishin N, it can be formed into solid preparations such as tablets, hard or soft capsules, granules, powder, fine particles or suppository; or into liquid preparations such as injection, syrups, elixirs, suspensions or emulsions, etc. Solid preparations may be prepared in the form of enteric coated preparations or gradually releasing preparations. As a carrier used for these preparations, there may be optionally selected depending on the desired type of preparations such as excipients, binders, disintegrants, lubricants, coating agents, dissolving adjuvants, emulsifiers, suspending agents, surfactants, absorption adjuvants, stabilizers or solvents, etc. Examples of carriers include starches, dextrins, $\alpha$, $\beta$ or $\gamma$-cyclodextrin, glucose, lactose, sucrose, mannitol, sorbitol, partially alpharized starch, methyl cellulose, ethyl cellulose, hydroxyethyl cellulose, carboxymethyl cellulose, calcium carboxymethyl cellulose, sodium cross-linked carboxymethyl cellulose, crystal cellulose, low-substitution degree hydroxypropyl cellulose, calcium stearate, magnesium stearate, sodium arginate, magnesium silicate, calcium hydrogen phosphate, calcium carbonate, magnesium carbonate, magnesium metasilicic aluminate, Witepsol W35, Witepsol E85, Witepsol H15, polyvinyl alcohol, silicic anhydride, synthesized aluminum silicate, titanium oxide, talc, waxes, hydroxypropyl cellulose, hydroxypropylmethyl cellulose, hydroxyethylmethyl cellulose, carboxymethylethyl cellulose, cellulose acetate phthalate, cellulose acetate maleate, hydroxypropylmethyl cellulose phthalate, hydroxypropylmethyl cellulose acetate succinate, polyvinylalcohol phthalate, styrene-maleic anhydride copolymer, polyvinylacetal diethylaminoacetate, methacrylic acid-methyl methacrylate copolymer, methacrylic acid-ethyl acrylate copolymer, methacrylic acid-butyl methacrylate and dimethylaminoethyl methacrylate copolymer, ethyl acrylatemethyl methacrylate and ammonium trimethyl chlorideethyl methacrylate copolymer, gelatin, glycerin, propylene glycol, sodium lauryl sulfate, medium chain aliphatic acid triglyceride, lecitin, sorbitan monooleate, sorbitan sesquioleate, polyoxyethylene sorbitan monooleate, glyceryl monostearate, glyceryl monooleate, polyoxyethylene cetyl ether, polyoxyethylene cured castor oil, cane sugar aliphatic acid ester, polyglycerin aliphatic acid ester, polyoxyethylenepolyoxypropylene block copolymer, polyethylene glycol, polyvinyl pyrrolidone, cross-linked polyvinyl pyrrolidone or oil and fats such as cocoa butter, laurin butter, and glycerogelatin, etc.

In the following, the present invention is explained in more detail by referring to examples of preparation methods of Saishin N and examples of compositions.

METHOD EXAMPLE 1

1500 g of Saishin was pulverized by an atomizer, and extracted with 4 liters of chloroform under heat-refluxing for one hour. This extraction step was repeated three times, and the extracts were combined and condensed under reduced pressure to obtain 93 g of an extract. Next, the extract was subjected to contact treatment by 2 liters of n-hexane three times in total to obtain 87 g of n-hexane-soluble extract. The extract was applied to column chromatography using 800 g of silica gel, and succesively eluted by using a mixed solution of n-hexane:ehtyl acetate while changing the mixing ratio thereof (volume ratio=50:1-10:1). Then, eluted portion by chloroform was collected and condensed under reduced pressure to obtain 4.48 g of crude product. This crude product was applied to column chromatography using 70 g of silica gel and eluted by using a mixed solution of benzene:acetone (volume ratio=60:1) succesively. Then, eluted portion by benzene:acetone (volume ratio=10:1) was collected and condensed under reduced pressure to obtain 730 mg of crude product. This was dotted on a silica gel thin layer plate for preparation with 30 mg per a plate and developed three times with benzene:acetone (volume ratio=9:1) and then developed once with a mixed solution of n-hexane:ethyl acetate:ethanol (volume ratio=4:1:1). Subsequently, Saishin N portion judged from UV absorption and coloring by anisaldehyde sulfuric reagent was scraped off and extracted with chloroform to obtain 72 mg of Saishin N.

IR Spectrum (KBr, cm$^{-1}$): 3450, 2980, 2950, 1680, 1450, 1370.

$^1$H-Nuclear magnetic Resonance Spectrum (CDCl$_3$, ppm): 6.50 (1H, m), 4.35 (1H, m), 3.22 (1H, d), 2.52 (1H, d), 2.34 (1H, d), 1.83 (3H, dd), 1.11 (3H, s), 1.01 (3H, S).

$^{13}$C-Nuclear magnetic Resonance Spectrum (CDCl$_3$, ppm): 19.09 (q), 22.86 (q), 27.73 (q), 34.50 (s), 54.54 (t), 69.94 (d), 81.15 (d), 138.34 (s), 145.36 (d), 201.57 (s).

METHOD EXAMPLE 2

4,5-Epoxy-2,6,6-trimethylcyclopenta-2-en-1-one

To a methylene chloride (20 ml) solution containing eucarvone (1.5 g, 10 mmole) dissolved therein was added m-chloroperbenzoic acid (2.37 g, 11 mmole) over 10 minutes at room temperature under stirring, and the mixture was stirred at room temperature for one hour. Precipitates were removed by filtration, and the filtrate was diluted with hexane, washed with a dil. aqueous sodium hydroxide solution and a saturated saline solution, dried over magnesium sulfate, filtered and then condensed. The residue after condensation was purified by silica gel column chromatography using hexane-isopropyl ether (5:1) as an eluent to obtain 1.56 g (Yield: 93%) of the colorless oily product of the headline.

$^1$H-Nuclear magnetic Resonance Spectrum (CDCl$_3$, ppm): 1.03 (3H, s), 1.27 (3H, s), 1.90 (3H, d J=2 Hz), 2.21 (1H, dd, J=13, 2 Hz), 2.89 (1H, d, J=13 Hz), 3.14 (1H, dd, J=4, 2 Hz), 3.34 (1H, dd, J=6, 4 Hz), 6.48 (1H, dq, J=6, 2 Hz)

Saishin N

Then, to a tetrahydrofuran (10 ml) solution containing the above epoxide (0.97 g, 5.8 mmole) dissolved therein was added a 10% perchloric acid (2 ml) under ice-cooling and stirring, and the mixture was stirred for 6 hours, followed by stirring at room temperature overnight. The reaction mixture was diluted by ethyl acetate, washed with a dil. aqueous sodium hydroxide solution and a saturated saline solution, dried over sodium sulfate, filtered and then condensed. The residue after condensation was purified by silica gel column chromatography using benzene-ethyl acetate (3:1) as an eluent, followed by crystallization from a mixed solution of benzene and hexane to obtain 598 mg (Yield: 56%) of Saishin N as a colorless plate crystal (melting point; 77.5° to 78.5° C.).

$^1$H-Nuclear magnetic Resonance Spectrum (CDCl$_3$, ppm): 1.01 (3H, s), 1.11 (3H, s), 1.83 (3H, dd, J=2.0, 1.5 Hz), 2.35 (1H, d, J=12 Hz), 2.52 (1H, d, J=12 Hz), 3.22 (1H, d, J=9 Hz), 4.35 (1H, d.quintet, J=9, 2.0 Hz), 6.50 (1H, m).

COMPOSITION EXAMPLE 1: (TABLETS)

| | weight (%) |
|---|---|
| (1) Saishin N | 30.0 |
| (2) Silicic anhydride | 20.0 |
| (3) Lactose | 10.0 |
| (4) Calcium carboxymethyl cellulose | 10.0 |

-continued

| | weight (%) |
|---|---|
| (5) Hydroxypropyl cellulose | 3.0 |
| (6) Polyoxyethylene (40) monostearate | 0.5 |
| (7) Crystalline cellulose | 26.0 |
| (8) Magnesium stearate | 0.5 |
| | 100.0 |

The above (1) and (2) were mixed, and after adding (3) to (5) to them, they were mixed. To the mixture was added an aqueous solution containing (6) dissolved therein, and the mixture was granulated and then dried. The resulting granules were regulated in particle size, (7) and (8) were further added to effect mixing and formulated under pressure to prepare tablets each having 250 mg.

COMPOSITION EXAMPLE 2: (HARD CAPSULES)

| | weight (%) |
|---|---|
| (1) Saishin N | 20.0 |
| (2) Silicic anhydride | 15.0 |
| (3) Corn starch | 20.0 |
| (4) Lactose | 40.5 |
| (5) Polyoxyethylene (20) sorbitan monooleate | 0.5 |
| (6) Hydroxypropyl cellulose | 3.0 |
| (7) Magnesium stearate | 1.0 |
| | 100.0 |

The above (1) and (2) were mixed and after adding (3), (4) and (6) to them, they were mixed. To the mixture was added and mixed ethanol containing (5) dissolved therein, and the mixture was dried to prepare granules. To the granules was added (7) and mixed, they were filled in a hard capsule to prepare hard capsules each containing 300 mg.

COMPOSITION EXAMPLE 3: (GRANULES)

| | weight (%) |
|---|---|
| (1) Saishin N | 10.0 |
| (2) Silicic anhydride | 7.5 |
| (3) Lactose | 69.5 |
| (4) Low substitution degree hydroxypropyl cellulose | 10.0 |
| (5) Polyvinylpyrrolidone | 2.0 |
| (6) Lauryl sodium sulfate | 1.0 |
| | 100.0 |

The above (1) and (2) were mixed, and after adding (3) to (5) to them, they were mixed. To the mixture was added a solution containing (6) dissolved therein, and the mixture was kneaded and granulated by using an extrusion granulating machine to prepare cylindrical granules.

COMPOSITION EXAMPLE 4: (SOFT CAPSULES)

| | weight (%) |
|---|---|
| (1) Saishin N | 25.0 |
| (2) Polyethylene glycol 400 | 67.0 |
| (3) Polyoxyethylene (20) sorbitan monooleate | 5.0 |
| (4) Purified water | 3.0 |
| | 100.0 |

The above (1) to (4) were thoroughly mixed under heating, and the dispersion obtained was filled in a soft capsule by the conventional method to prepare soft capsules each containing 400 mg.

COMPOSITION EXAMPLE 5: (SUPPOSITORY)

|  | weight (%) |
|---|---|
| (1) Saishin N | 5.0 |
| (2) Wiptesol H15 | 85.0 |
| (3) Lauric acid triglyceride | 9.0 |
| (4) Lecitin | 1.0 |
|  | 100.0 |

The above (1) to (4) were thoroughly mixed under heating, and cooled to solidify them. It was melted at 50° to 60° C. and after cooling to 32° to 35° C., injected to a suppository mold, allowed to stand for cooling and solidified to prepare suppositories each having 2 g.

What is claimed is:

1. 4,5-Dihydroxy-2,6,6-trimethyl-2-cyclohepten-1-one.

2. Antiulcer agent containing 4,5-dihydroxy-2,6,6-trimethyl-2-cyclohepten-1-one as effective ingredient.

3. A method for preparing 4,5-dihydroxy-2,6,6-trimethyl-2-cyclohepten-1-one which comprises: oxidizing 2,6,6-trimethylcyclohepta-2,4-dien-1-one by peracid or oxygen to prepare 4,5-epoxy-2,6,6-trimethylcyclohept-2-en-1-one, and then, applying to acid-catalysed hydrolysis to open epoxide.

* * * * *